(12) United States Patent
Kreuzer et al.

(10) Patent No.: US 7,678,335 B2
(45) Date of Patent: Mar. 16, 2010

(54) DEVICE FOR SIMULTANEOUS MULTIPLE AND HIGH PARALLEL SYNTHESIS

(75) Inventors: Oliver Johannes Kreuzer, Berlin (DE); Carsten Hessenius, Berlin (DE); Carsten Grotzinger, Berlin (DE); Volker Johannson, Hamburg (DE); Ralph-Th. Roeder, Potsdam (DE)

(73) Assignee: Protein Technologies, Inc., Tucson, AZ (US)

( * ) Notice: Subject to any disclaimer, the term of this patent is extended or adjusted under 35 U.S.C. 154(b) by 1103 days.

(21) Appl. No.: 10/466,709

(22) PCT Filed: Apr. 25, 2002

(86) PCT No.: PCT/DE02/01556

§ 371 (c)(1),
(2), (4) Date: Aug. 9, 2004

(87) PCT Pub. No.: WO03/000403

PCT Pub. Date: Jan. 3, 2003

(65) Prior Publication Data

US 2004/0244867 A1   Dec. 9, 2004

(30) Foreign Application Priority Data

Jun. 25, 2001   (DE) ................. 101 31 088

(51) Int. Cl.
  *B01L 99/00*   (2006.01)
(52) U.S. Cl. .................. 422/101; 422/103; 422/100
(58) Field of Classification Search ............... 422/100, 422/101, 103, 104
See application file for complete search history.

(56) References Cited

U.S. PATENT DOCUMENTS

| 1,686,188 A | | 10/1928 | Tipton |
| 5,260,028 A | * | 11/1993 | Astle ........................... 422/81 |
| 5,551,487 A | | 9/1996 | Gordon et al. ................. 141/1 |

FOREIGN PATENT DOCUMENTS

EP   0 355 266   2/1990

* cited by examiner

*Primary Examiner*—Jill Warden
*Assistant Examiner*—Natalia Levkovich
(74) *Attorney, Agent, or Firm*—Quarles & Brady LLP; Gavin J. Milczarek-Desai

(57) ABSTRACT

This invention relates to an apparatus for simultaneously carrying out multiple and highly parallel synthesis of compounds based on the solid-phase synthesis technique, in particular, peptide synthesis.

Figure 1:
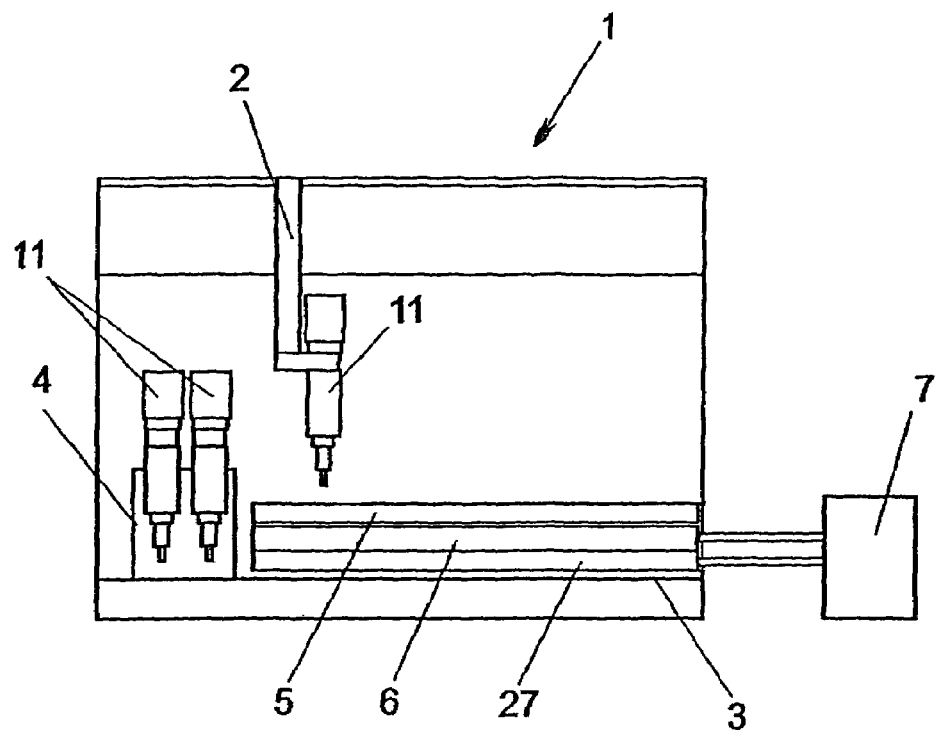

Time-consuming and costly multiple rinsing processes required in solid-phase synthesis after distributing and replacing the reagents can be avoided by proposing an improved apparatus for fully automatic synthesis and subsequent separation of the synthesized compounds that involves separate synthesizer pins 11 for each synthetic unit with a reagent reservoir 20; 21 and individual dosing capability. These synthesizer pins 11 are provided in a separate holder 4 from where they are picked up by the gripper arm 2 of the automatic synthesizer 1. The openings of the reaction chambers 9 of the synthesizer plates 5 are closed (covered) by a permeable material 25 for contamination-free placement of the synthesizer pins 11 and adding reagent doses to the solid or liquid phases. In addition, a sample plate 27 that collects the samples dissolved after separation is provided underneath the valve block 6 (see FIG. 1).

4 Claims, 2 Drawing Sheets

DEVICE FOR SIMULTANEOUS MULTIPLE AND HIGH PARALLEL SYNTHESIS

This invention relates to an apparatus for simultaneously carrying out multiple and highly parallel synthesis of compounds based on the solid-phase synthesis technique, in particular, peptide synthesis.

Numerous apparatuses are known for organic solid-phase synthesis processes of peptides in which, unlike in classical synthetic processes, many different synthetic units (amino acids) are linked together and coupled with a functional carrier in one process step, apparatuses that allow automatic simultaneous and parallel synthesis of more than 100 different peptides (see WO 98/35753; DE 196 02 464 A1).

These known apparatuses are designed like pipetting robots in which the reagents and solvents are transferred from storage reservoirs via one or more tubules attached to an arm of the synthesizing apparatus that can be moved along x, y, and z axes to the reaction chambers, and added in doses to the carrier material for the synthesis to be carried out.

WO 98/35753 proposes an apparatus for automated chemical synthesis to produce biomolecules in which the reagents are dispensed using a set of multiple tubules. This set of multiple tubules has to be rinsed after distributing each synthetic unit to exclude contamination of reagents.

For a synthesis involving 48 different peptides and a chain length of 10 synthetic units, the net rinsing time required is 8 hours, and each rinsing process takes one minute. For 96 peptides, rinsing time is 16h, for 384 peptides 64h, and for 1536 peptides 256h. This means that synthesis cannot be carried out at a high degree of parallelism.

Some publications describe the use of synthesizer plates derived from microtitration breadboards with a grid of 96 or 384. These are placed onto a valve block which vacuums off any unused reagents as well as the rinsing fluids and separation solutions for the temporary protective groups using a vacuum pump. As shown in DE 197 44 549 A1 and elsewhere, the reaction chamber is closed by a membrane at its bottom to allow the reaction fluids to be vacuumed off.

Despite the major advantages these apparatuses hold for automated, simultaneous, multiple and parallel synthesis, a decisive disadvantage is that various reagents are discharged through the same hose systems and tubules, which creates the risk of cross-contamination. To exclude contamination, the known apparatuses use generous quantities of rinsing agents to rinse the entire system. In addition to the material cost for the rinsing agent, synthesis time is considerably extended due to the required rinsing processes. Another disadvantage of the known apparatuses is that these feature open pipetting systems and do not allow an inert gas atmosphere for pre-activated reagents. Increased instability and, consequently, increased consumption of reagents as well as the need for manual reagent replacement result from this.

Another synthesizing apparatus is known from DE 198 18 999 A1. The carrier material for the synthesis is applied to a rotating drum or disk and features so-called spots for absorbing the reagents. A dosing head holder that can be adjusted in linear or radial direction to the drum's axis and holds multiple pipette-shaped dosing heads dispenses doses of the reagents supplied via hoses from a reservoir to the respective spot. However, this apparatus has similar disadvantages as described above. Furthermore, the hose connections required here make handling more complex and difficult. While this solution eliminates the need for the rinsing steps for distributing synthetic components, synthesis is not carried out in reaction chambers but take place on a planar carrier such as a sheet of foil or paper, or on glass slide. Synthesis on a larger scale is not possible, and no flexible carriers but only carriers for planar application can be used.

The state of the art further includes an ink writer for drawing ink instruments and marker pens for applying doses of a liquid incorporated in the instrument or marker body onto a substrate they are placed on. Such equipment is not known in laboratory practice or for use in solid-phase or liquid-phase synthesis and other methods of chemical or biological examination and analysis.

It is the problem of this invention to develop an improved apparatus for the automated synthesis of compounds that eliminates the rinsing processes required as yet after reagent distribution or replacement, and that combines supply, dosing, and reagent storage in a single component for each synthetic unit. In addition, synthesis, separation of compounds from synthetic resin and unprotecting of lateral chains—as yet requiring separate apparatuses each—shall all be carried out in a single, fully automated apparatus.

This problem is solved according to the invention by an apparatus featuring the characteristics listed in claim 1. Advantageous improvements of the invention result from the characteristics listed in subclaims 2 through 8.

The invention proposes an apparatus that does completely without diluents and hose systems for supplying and dispensing synthetic units. Separate synthesizer pins are provided for each synthetic unit in a holder of the synthesizer and can be picked up from there by a gripper arm of the apparatus to dispense a dosed quantity of each unit onto the carrier material located in a reaction chamber of a synthesizer plate. Reagent reservoir and dosing apparatus thus form a self-contained unit. This eliminates the need for any rinsing and the disadvantages resulting from it whenever synthetic units are changed or reagents are distributed.

The synthesizer plate has a modular design and consists of ten individual plates containing reaction chambers. These have a 96, 384, or 1536 breadboard grid like microtitration plates. According to further characteristics of the invention, the openings of the reaction chambers of the synthesizer plates are closed using a permeable material such as a frit. Sample coupons for collecting the dissolved samples after the separation reaction are located underneath the valve block and connected to an extraction system. The proposed apparatus for solid-phase synthesis allows both synthesis and separation of the synthesized compounds from the carrier material, a synthetic resin, without requiring any manual interference.

The sample plates are equipped with individual holding chambers whose array and shape correspond to the grid of reaction chambers in the synthesizer plate. In this way each compound can be identified easily and without errors after being separated from the synthetic resin. Direct transfer of the reaction products to high-throughput screening routes this becomes an easy option.

The synthesizer pin has a hollow cylindrical body that can be screwed shut and a mouthpiece at its bottom that can be adjusted to the free opening of the reaction chambers in the synthesizer plate and has an outlet aperture. This outlet aperture is closed by a valve needle with a check valve that runs through a piston rod and a piston in the body where it is detachably fixed in its closing position using a pressure spring that acts on the piston. The cylinder space underneath the piston is used to hold one single synthetic unit and an inert gas, and the reagent is dispensed in doses by simply placing the mouth-piece on the permeable material that covers the opening side of the reaction chamber. This also pushes the valve needle into the body and releases the check valve from its seat to open up the outlet aperture. The quantity of the reagent dispensed depends on the time the mouthpiece remains sitting upon the permeable material. When the mouthpiece is lifted away, the opening aperture is automatically sealed again.

The enclosed design of the synthesizer pin with a sealed reagent reservoir ensures a high degree of reagent stability. The risk of contamination is considerably reduced, and cross-contamination virtually excluded, by using separate synthesizer pins for each synthetic unit and by covering the opening of the reaction chamber in the synthesizer plates. Synthetic units can no longer be retained in the system as it did happen when conventional systems were not sufficiently rinsed.

The elimination of the rinsing processes does not only reduce the consumption of organic solvents considerably but also accelerates synthesis itself.

Figure 2:
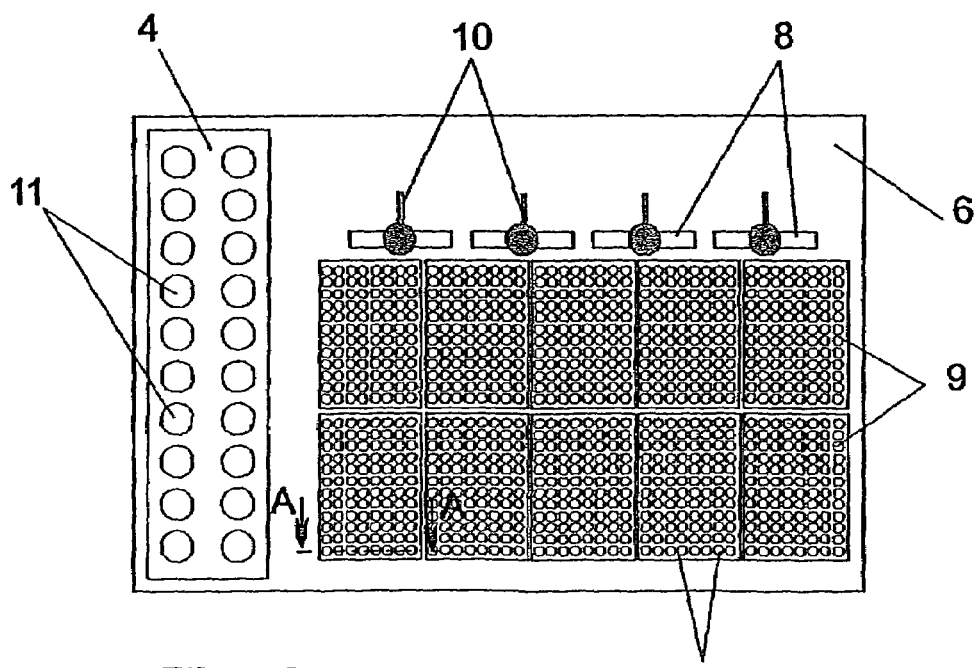
Figure 5:
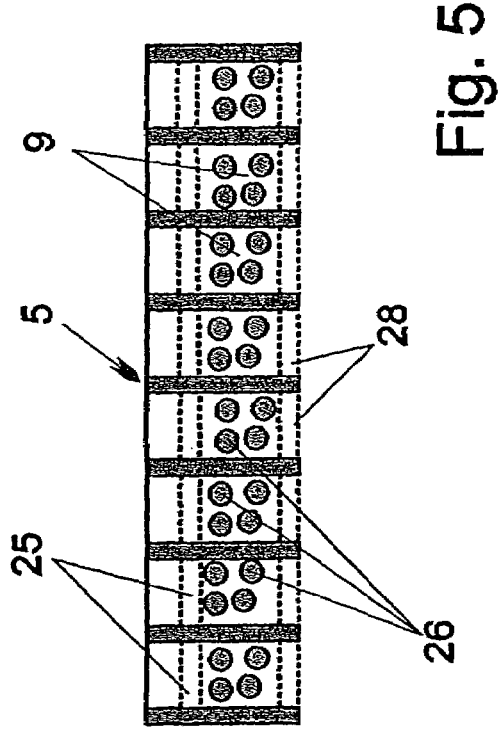
Figure 4:
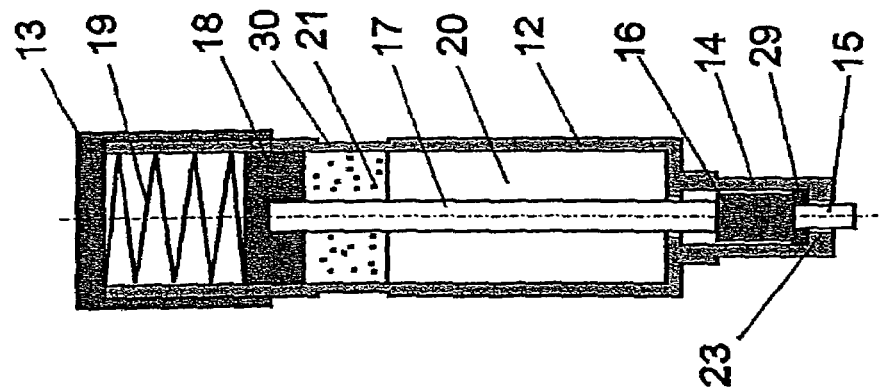
Figure 3:
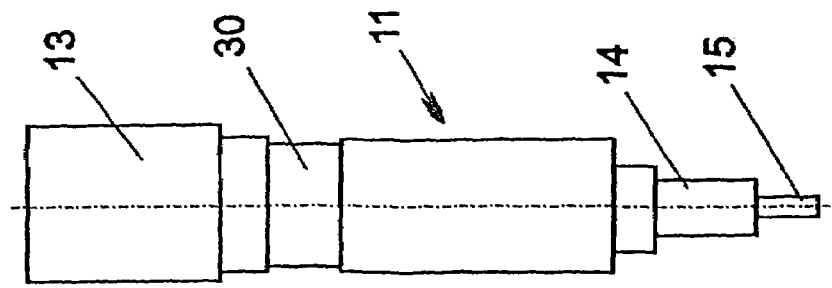

The invention will be explained in greater detail with reference to an embodiment below. The associated figures show the following:

FIG. 1: a schematic representation of the apparatus according to the invention for synthesizing compounds, FIG. 2: a top view of the working surface of the apparatus shown in FIG. 1, FIG. 3: a schematic representation of the synthesizer pin for separate reagent supply, dosage, and storage, FIG. 4: a longitudinal section through the synthesizer pin shown in FIG. 3, FIG. 5: a sectional view along the line A-A in FIG. 2 through a synthesizer plate with reaction chambers according to the invention.

The synthesizing apparatus 1 that is schematically represented in FIG. 1 is designed based on a pipetting robot and comprises a gripper arm 2 that can be moved along x, y, and z axes. The working surface 3 comprises synthesizer plates 5 whose grid and array of reaction chambers 9 is derived from generally known microtitration plates, said reaction chambers 9 having a 96, 384 or 1536 grid, which provides a high degree of parallelism for the synthesis. The synthesizer plates 5 are set upon a valve block 6 and comprise a membrane 28 made of a porous material on their bottom sides for discharging used reagents and rinsing liquids from the reaction chambers 9 using the valve block 6 that is connected to a vacuum pump.

The synthesizing apparatus 1 further comprises multiple rinsing combs 8 that are connected to their respective rinsing agent tank via rinsing agent supply lines 10. The rinsing comb 8 with the required rinsing agent is picked up by the gripper arm 2 which then moves to dispense rinsing fluid across the reaction chambers 9 of the synthesizer plates 5 to rinse the samples in the reaction chambers 9 to which a synthetic unit was linked after reaction time has elapsed and the used reaction solution been vacuumed off. After rinsing, another rinsing comb 8 supplies the solution required to separate the temporary protective group from the synthetic unit linked to the sample. After the incubation period, the separation solution is discharged via the valve block 6 using the vacuum pump 7, and the sample is washed. A new synthesis cycle starts after washing, and another synthetic unit is linked to the sample.

According to the present invention, separate synthesizer pins 11 are provided for each synthetic unit in which the reagents are supplied in an enclosed space and can be covered with a layer of an inert gas 21. The individual synthesizer pins 11 and their respective synthetic unit are provided in a holder 4 of the synthesizing apparatus 1, picked up by a gripper arm 2 in the grip section 30 and taken to the reaction chamber 9 of synthesizer plates 5 for dispensing doses of the reagents.

The synthesizer pin 11 according to the invention consists of a hollow cylindrical body 12 with a mouthpiece 14 at its foot and a screw-type cap 13 that seals off the cylinder space. The mouthpiece 14 comprises an outlet aperture which is closed by a valve needle 15 and a check valve 16 that sits on a sealing 29 in closed position. The valve needle 15 and check valve 16 are guided by a piston 18 using a piston rod 17. The closing pressure required for the check valve 16 is produced by a pressure spring 19 that sits on the piston 18 and is supported by the inner surface of the screw-type cap 13. The free space under the piston 18 is used for providing the respective synthetic unit 50 which is preferably covered with a layer of an inert gas 21. In this way, highly reactive reagents can be kept stable in an inert gas atmosphere for longer periods of time, which considerably improves the quality of the synthetics.

To prevent cross-contamination when the mouthpiece 14 is in direct contact with the sample, the openings of the reaction chambers 9 that contain the samples or solid phase 26 such as a synthetic resin, respectively, are covered by a permeable material such as a frit. When linking a synthetic unit to the sample or synthetic resin, the mouthpiece 14 of the synthesizer pin 11 is placed upon the permeable material 25 that closes the reaction chamber, which pushes the valve needle 15 inwards against the pressure from the pressure spring 19 so that the check valve 16 is released. This freely dispenses the reagent solution whose dosage depends on the length of time the mouthpiece 14 remains set upon the material 25.

When the temporary protective group is separated and the samples are washed, the synthetic units linked to the solid phase 26 are also split off. The rinsing comb 8 adds a separating solution to the samples and initiates a split-off reaction. When the incubation time has elapsed, the valve block 6 is switched in such a way that the compounds dissolved in the separating solution are conducted to the collecting chambers of a sample coupon 27 that is located underneath valve block 6 according to yet another characteristic of the invention and connected to an extraction system. These sample coupons 27 have a similar shape and design as the synthesizer plates 5. Synthesis is completed when the compounds dissolved by the solid phase 26 are transferred into the sample coupon 27.

LIST OF REFERENCE SYMBOLS

1 Synthesizing apparatus
2 Gripper arm
3 Working surface
4 Holder
5 Synthesizer plate
6 Valve block
7 Suction pump
8 Rinsing comb
9 Reaction chambers
10 Rinsing agent supply line
11 Synthesizer pin
12 Body
13 Screw-type cap
14 Mouthpiece
15 Valve needle
16 Check valve
17 Piston rod
18 Piston
19 Pressure spring
20 Reagent Reservoir
21 Inert gas
22 -
23 Outlet aperture 24 -
25 Permeable material/frit
26 Solid phase
27 Sample coupon
28 Membrane
29 Packing
30 Gripper arm receptacle

We claim:

1. An apparatus for simultaneous multiple and high-throughput synthesis of peptides and other molecules based on the solid-phase synthesis technique comprising:
   an automated synthesizer comprising a gripper arm that can be moved along x, y, and z axes and is disposed above a working surface on a base of said automated synthesizer,
   a synthesizer plate located on said working surface of the apparatus,
   a plurality of separate synthesizer pins (11), each pin including a reagent reservoir (20) that contains a given synthetic unit 50,
   a holder (4) that holds said plurality of synthesizer pins upon said working surface,
   a plurality of reaction chambers (9) disposed on said synthesizer plate, the reaction chambers each having an opening at its top side, and a permeable material (25) comprising a frit and configured to close said opening, and further including a porous membrane (28) disposed at a bottom side of each of said reaction chambers,
   a sample coupon (27) that is disposed underneath the synthesizer plate to collect a dissolved sample after separation, and
   a valve block for collecting and discharging rinsing solutions, wherein the valve block is disposed upon said working surface between said synthesizer plate and said sample coupon.

2. The apparatus according to claim 1, characterized in that the synthesizer pins (11) comprise a hollow cylindrical body (12) with a screw-type cap (13) and a mouthpiece (14) on its foot, and in that said mouthpiece (14) comprises an outlet aperture (23) that is closed using a valve needle (15) with a check valve (16) guided by a piston rod (17) and a piston (18) and detachably fixed in closed position by a pressure spring (19) acting on said piston (18) while the cylinder space underneath said piston (18) is used to hold a synthetic unit in said reagent reservoir (20) and an inert gas (21).

3. The apparatus according to claim 1, characterized in that plates with a 96, 384, or 1536 grid of reaction chambers (9) are used as synthesizer plates (5), and that the sample coupon (27) is equipped with holding chambers whose arrangement and shape corresponds to the 96, 384, or 1536 grid of reaction chambers (9) in the synthesizer plate (5).

4. The apparatus according to claim 1, characterized in that the sample coupons (27) are connected to an extraction system (7).

* * * * *